(12) United States Patent
Edgson et al.

(10) Patent No.: US 6,818,179 B1
(45) Date of Patent: Nov. 16, 2004

(54) METHOD AND APPARATUS FOR STERILIZING A HEAT SENSITIVE FLUID

(75) Inventors: Raymond Anthony Edgson, Litlington (GB); Michael John Dunkley, Cambridge (GB); Richard J. Hammond, Cambridge (GB); Eric Wilkinson, Cambridgeshire (GB)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 09/937,738

(22) PCT Filed: Mar. 30, 2000

(86) PCT No.: PCT/SE00/00614

§ 371 (c)(1),
(2), (4) Date: Apr. 15, 2002

(87) PCT Pub. No.: WO00/57928

PCT Pub. Date: Oct. 5, 2000

(30) Foreign Application Priority Data

| Mar. 30, 1999 | (SE) | ................................................ 9901165 |
| Sep. 16, 1999 | (SE) | ................................................ 9903331 |

(51) Int. Cl.[7] ................................................ A61L 2/00
(52) U.S. Cl. .............................. 422/38; 210/143; 422/1; 422/41; 422/307; 422/308
(58) Field of Search ................................ 422/38, 41, 1, 422/307, 308; 210/143, 149; 426/521, 522; 99/483

(56) References Cited

U.S. PATENT DOCUMENTS

| 4,393,088 | A | * | 7/1983 | Matsusaka ................... 426/234 |
| 4,542,034 | A | * | 9/1985 | Aule et al. .................... 426/522 |
| 4,975,246 | A | * | 12/1990 | Charm .......................... 422/21 |
| 5,476,592 | A | * | 12/1995 | Simard ......................... 210/651 |
| 5,539,673 | A | * | 7/1996 | Charm et al. ................ 700/299 |
| 5,603,894 | A | | 2/1997 | Aikus et al. ................... 422/23 |
| 6,579,494 | B1 | * | 6/2003 | Chevallet et al. .............. 422/3 |

FOREIGN PATENT DOCUMENTS

| EP | 0 428 009 A1 | 5/1991 |
| GB | 1450030 | 9/1976 |
| GB | 1504334 | 3/1978 |
| GB | 2034584 A | 6/1980 |
| WO | 93/09820 | 5/1993 |
| WO | 96/13279 | 5/1996 |
| WO | 98/07328 | 2/1998 |
| WO | 99/27885 | 6/1999 |
| WO | 00-24433 | 5/2000 |

* cited by examiner

Primary Examiner—Krisanne Jastrzab
(74) Attorney, Agent, or Firm—Lerner, David, Littenberg, Krumholz & Mentlik, LLP (57) ABSTRACT

Methods and apparatus for sterilizing heat sensitive fluids are provided. The methods include providing a first heat sensitive fluid component, providing a second fluid component, heating the second fluid component to a temperature greater than a predetermined sterilizing temperature, mixing the first heat sensitive fluid component with the heated second fluid component to heat the first heat sensitive fluid components and provide a mixed fluid at a temperature at least up to the predetermined sterilizing temperature, and maintaining the mixed fluid at that temperature for a predetermined sterilizing period. Apparatus for carrying out this method is also provided.

44 Claims, 4 Drawing Sheets

METHOD AND APPARATUS FOR STERILIZING A HEAT SENSITIVE FLUID

FIELD OF INVENTION

The present invention relates to a method and apparatus for producing a sterile medical solution. More specifically, the present invention relates to a method and apparatus for producing a sterile medical solution comprising a heat sensitive component, such as glucose.

BACKGROUND OF THE INVENTION

Medical solutions intended for mammals, specifically for use in humans, are required to be sterile before being infused or applied to the mammal.

One available method for sterilizing a solution is to heat the solution to a sterilizing temperature and to hold the solution at the sterilizing temperature during a sterilizing time period. To obtain a sterile medical solution intended for infusion, the solution is normally heated in an autoclave to 121° C. for 20 minutes to thereby produce said sterile medical solution. After the sterilizing time has elapsed, the solution should be cooled to a physiologically acceptable temperature before infusion.

Known methods and apparatus for sterilizing a solution are disclosed, for example, in British Patent Applications Nos. 1,450,030; 1,504,334; and 2,034,584, and in U.S. Pat. No. 5,603,894. These prior art publications describe the preparation of a medical solution starting from tap water and producing pure water by means of a reverse osmosis device, mixing a concentrate with the pure water to produce a non-sterile medical solution, passing the non-sterile medical solution through an on-line autoclave and delivering the sterile medical solution to a recipient, such as a storage bag or a patient.

In the prior art, the complete medical solution is first prepared in a non-sterile condition and then passes through an autoclave. If the medical solution comprises heat sensitive components, these must not be exposed to too high a temperature. Normally, the temperature is increased up to the sterilizing temperature and the medical solution is maintained at the sterilizing temperature for a sterilizing time period. If the temperature is 121° C., which is normal in an autoclave, the sterilizing time is 20 minutes to obtain a sterilizing dose, $F_0$, of 20 minutes, as discussed below. Since the sterilizing effect is approximately exponential, an increase of the temperature by 10° C. means a lowering of the sterilizing time by ten times. If a sterilizing temperature of 131° C. is used, the sterilizing time should be 2 minutes, and if a sterilizing temperature of 141° C. is used, the sterilizing time should be 12 seconds, in order to obtain a sterilizing effect, $F_0$, of 20 minutes.

If the medical solution comprises a heat sensitive component, like glucose, that component will deteriorate during the heat treatment. An example of a medical solution containing a heat sensitive component is a dialysis fluid for peritoneal dialysis (PD). The decomposition or heat deterioration starts at a much lower temperature than the sterilizing temperature and is also present at room temperature. In order to safeguard the heat sensitive material, very short heating and cooling periods are desired so that the time/temperature profile becomes more or less rectangular. This is of greater importance if high sterilizing temperatures and short sterilization times are used.

It is known to produce sterile medical solutions by including the medical solution in a bag and placing the bag inclusive of the medical solution, in an autoclave for heating and sterilization.

A variant of this method is described in international Application No. WO 93/09820, in which the medical solution is divided into two portions, one comprising glucose at high concentration and the other comprising the rest of the solution. The double bag is heat sterilized in an autoclave. Shortly before use, the contents of the two chambers are mixed to produce the sterile medical solution. In this way, the heat sensitive component, glucose, can be autoclaved under more appropriate conditions, such as at a low pH of approximately 3.2, and at a high concentration of approximately 50%, i.e. 500 grams of glucose per liter of glucose solution.

A variant of the same methods is described in International Application No. WO 97/05852 disclosing a three-chamber-bag, in which two of the chambers comprise glucose solution and the third chamber comprises the rest of the solution. The glucose chambers may also include ionic components, such as calcium, magnesium and sodium.

A further variant is described in International Application No. WO 99/27885.

In the aforementioned concepts, the glucose portion is sterilized separately from the remaining portion of the solution. However, in order to fully sterilise the large compartment, the small glucose compartment may be over sterilized, resulting in deterioration of the heat sensitive component. A remedy for that problem is described in Swedish patent application No. 9803627-0, filed at the Swedish Patent Office on Oct. 23, 1998.

The problem of deterioration of a substance during autoclaving is also recognised in other fields of use, such as the production of sterile milk products. In order to obtain rapid heating and cooling of the product, it is not sufficient to use heat transfer by means of a heat transferring surface, like a heat exchanger. Instead, the product is mixed with steam at a predetermined temperature and pressure to condense the steam in the milk product. The milk product is sterilized by retention in a holding zone for a certain time period and at a temperature of from about 120 to 150° C., and is then transferred to a flash cooling step, in which water is evaporated in an evaporation chamber to rapidly cool the product. Such a process is described in, for example, International Application No. WO 98/07328.

DISCLOSURE OF INVENTION

One object of the present invention is to provide a method and apparatus for producing a sterile medical solution having a gentle treatment of the heat sensitive component.

Another object of the present invention is to provide a method and apparatus in which inexpensive heaters and heat exchangers can be used.

A third object of the present invention is to provide a method and apparatus for sterilizing a medical solution in which the time/temperature profile for heating the heat sensitive component is essentially rectangular.

SUMMARY OF THE INVENTION

In accordance with the present invention, these and other objects have now been realized by the invention of a method for sterilizing a heat sensitive fluid comprising providing a first heat sensitive fluid component, providing a second fluid component, heating the second fluid component to a first temperature, the first temperature being greater than a predetermined sterilizing temperature, mixing the first heat sensitive fluid component with the heated second fluid component, whereby the first heat sensitive fluid component is heated and the heated second fluid component is cooled, and a mixed fluid is provided at a second temperature, the second temperature being at least the predetermined sterilizing temperature, and maintaining the mixed fluid at the second temperature for a predetermined sterilizing period, whereby a predetermined sterilizing dose is obtained for delivery to a recipient. Preferably, the method includes controlling the heating of the second fluid component to the first temperature to ensure that the mixed fluid reaches the second temperature.

In accordance with one embodiment of the method of the present invention, the method includes cooling the mixed fluid.

In accordance with another embodiment of the method of the present invention, the first heat sensitive fluid component comprises glucose or a glucose polymer.

In accordance with another embodiment of the method of the present invention, the second fluid component comprises water. Preferably, the second fluid component includes electrolytes, such as sodium chloride, calcium chloride, magnesium chloride, potassium chloride, sodium bicarbonate, or sodium lactate.

In accordance with another embodiment of the method of the present invention, the method includes preheating the first heat sensitive fluid component.

In accordance with another embodiment of the method of the present invention, the method includes maintaining the first heat sensitive fluid component and the second fluid component under a predetermined pressure sufficient to prevent boiling of the first heat sensitive fluid component and the second fluid component. Preferably, providing of the first heat sensitive fluid component and providing of the second fluid component comprises providing flows of these fluid components. In a preferred embodiment, the flow of the first heat sensitive fluid component comprises a first flow rate and the flow of the second fluid component comprises a second flow rate, the second flow rate being greater than the first flow rate.

In accordance with another embodiment of the method of the present invention, the method includes determining the first and second flow rates by means of a weighing device or a flow meter, and maintaining the first heat sensitive fluid component and the second fluid component at the predetermined pressure by means of a pump.

In accordance with another embodiment of the method of the present invention, the heat sensitive fluid component comprises a complex fluid comprising a plurality of first fluid components including the first heat sensitive fluid component, and the method includes sequentially sterilizing the plurality of first fluid components. In a preferred embodiment, the method includes providing a plurality of sources of concentrate fluid components for each of the plurality of first fluid components, providing a source of the second fluid component, the second fluid component comprising water, pumping one of the plurality of sources of the concentrate fluid components so as to increase the pressure thereof, pumping the water so as to increase the pressure thereof, and repeating the method for each of the plurality of first fluid components. Preferably, the method includes preheating each of the plurality of first fluid components before the mixing with the heated second fluid component. Most preferably, the preheating comprises heat exchanging each of the plurality of the first fluid components with the predetermined sterilized dose. Preferably, the preheating comprises initially heating the second fluid component by heat exchange with the predetermined sterilized dose, and further preheating the second fluid component to the first temperature by means of a separate heater, preferably comprising an electric heater. Preferably, the method includes controlling the further preheating of the second fluid component by means of a temperature sensor downstream of the maintaining of the mixed fluid at the second temperature, whereby the second temperature is maintained at the at least the predetermined sterilizing temperature.

In accordance with another embodiment of the method of the present invention, the method includes dissolving at least one powdered substance in the second fluid component to provide at least one of the first heat sensitive fluid components and the second fluid component.

In accordance with another embodiment of the method of the present invention, the method includes providing a third heat sensitive fluid component, and mixing the first heat sensitive fluid component and the third heat sensitive fluid component with the heated second fluid component. Preferably, the third heat sensitive fluid component comprises water and at least one amino acid.

In accordance with the present invention, an apparatus has also been discovered for sterilizing a heat sensitive fluid comprising a first vessel containing a first heat sensitive fluid component, a second vessel containing a second fluid component, a first heater for heating the second fluid component to a first temperature, the first temperature being greater than a predetermined sterilizing temperature, mixing means for mixing the first heat sensitive fluid component with the second fluid component to obtain a mixed fluid at a second temperature at least equal to the predetermined sterilizing temperature, and residence means for maintaining the mixed fluid at the second temperature for a predetermined sterilizing period, whereby a sterilized fluid is provided for delivery to a recipient. Preferably, the apparatus includes a controller for controlling the first heater to obtain the first temperature.

In accordance with one embodiment of the apparatus of the present invention, the apparatus includes a cooler for cooling the mixed fluid.

In accordance with another embodiment of the apparatus of the present invention, the first heat sensitive fluid component comprises glucose or a glucose polymer.

In accordance with another embodiment of the apparatus of the present invention, the second fluid component comprises water. Preferably, the second fluid component includes an electrolyte, including sodium chloride, calcium chloride, magnesium chloride, potassium chloride, sodium bicarbonate or sodium lactate.

In accordance with another embodiment of the apparatus of the present invention, the apparatus includes a preheater for preheating the first heat sensitive fluid component.

In accordance with another embodiment of the apparatus of the present invention, the apparatus includes pressurizing means for maintaining the first heat sensitive fluid component and the second fluid component at a predetermined pressure to prevent the first heat sensitive fluid component and the second fluid component from boiling.

In accordance with another embodiment of the apparatus of the present invention, the first heat sensitive fluid component and the second fluid component comprise fluid flows. Preferably, the fluid flow of the first heat sensitive fluid component has a first flow rate and the fluid flow of the second fluid component has a second flow rate, the second flow rate being greater than the first flow rate. Preferably, the apparatus includes flow rate determining means for determining the first and second flow rates, the pressurizing means comprising a pump. Preferably, the flow rate determining means comprises a weighing device or a flow meter.

In accordance with another embodiment of the apparatus of the present invention, the first heat sensitive fluid component comprises a plurality of first fluid components including the first heat sensitive fluid component, and the apparatus includes means for sequentially sterilizing each of the plurality of first fluid components and the second fluid component. In a preferred embodiment, the means for sequentially sterilizing includes supply means for supplying the plurality of first fluid components, the first vessel comprising a plurality of containers for concentrates of the plurality of first fluid components, the second vessel comprising an inlet for the second fluid component, a concentrate pump for pumping one of the plurality of first fluid components from one of the plurality of containers whereby the pressure of the one of the first fluid components is increased, a water pump for pumping the second fluid component, the second fluid component comprising water, whereby the pressure of the second fluid component is increased, the heater comprising a water heater for heating the second fluid component to the first temperature, the mixing means comprising a mixer for mixing the one of the plurality of first fluid components and the heated second fluid component to provide said mixed fluid, the residence means comprising means for maintaining the mixed fluid at the first temperature for a predetermined sterilizing period to provide a sterilized dose for delivery to a recipient, and including control means for controlling and repeating the sequential sterilizing of each of the plurality of first fluid components to provide a final sterilized complex fluid. Preferably, the apparatus includes preheating means for preheating the one of the plurality of first fluid components. Most preferably, the apparatus includes a heat exchanger for recovering heat from the sterilized dose, the heat exchanger preheating the second fluid component by heat exchange with the sterilized dose, and the apparatus including a heater for heating the second fluid component to the first temperature. Most preferably, the apparatus includes a temperature sensor downstream of the residence means for controlling the heater, whereby the first temperature comprises a temperature at least sufficient to constitute the sterilizing temperature.

In accordance with another embodiment of the apparatus of the present invention, at least one of the first and second vessels includes at least one powdered substance for dissolution in water to provide at least one of the first and second fluids.

In accordance with another embodiment of the apparatus of the present invention, the apparatus includes a third vessel for containing a third heat sensitive fluid component. Preferably, the third heat sensitive fluid component comprises water and at least one amino acid.

According to the present invention, a method of sterilizing a heat sensitive fluid is provided, comprising providing the fluid as a first heat sensitive component and a second less heat sensitive component; heating the second component to a first temperature higher than a predetermined sterilizing temperature; mixing the first component with the second component to thereby heat the first component and cool the second component, whereby the mixed components obtain a mixing temperature, which is at least equal to the sterilizing temperature; maintaining the mixed components at substantially the sterilizing temperature during a sterilization time period, so that a predetermined sterilization dose is obtained; and delivering the mixed component to a recipient.

Preferably, the first temperature is controlled to obtain a mixing temperature, which is at least equal to the sterilizing temperature. Moreover, it is preferred to cool the mixed components before delivery to the recipient.

The first heat sensitive component may comprise glucose or a glucose polymer and the second less heat sensitive component may comprise water. More specifically, the second component may include electrolytes, selected from the group of substances comprising: sodium chloride, calcium chloride, magnesium chloride, potassium chloride, sodium bicarbonate and sodium lactate.

It may be advantageous to preheat the first component. Normally, the temperature is above the boiling temperature at normal atmospheric pressure and, thus, the first and second components are maintained at a high pressure sufficient to prevent boiling.

In one embodiment, the first and second components are provided as flows of fluid, in which the flow rate of the second component is larger than the flow rate of the first component.

In order to separate the flow rate determination from the pressurising means, the flow rates are determined with a pair of scales or a flow meter, and the pressure is provided by a separate pump.

In one embodiment of the present invention, the complex fluid is divided into several fluid components, which are sterilized separately, as described above, and sequentially and then mixed with the complex fluid. This may be performed by providing sources of concentrated fluid components and pure water; pumping a first concentrated fluid from the sources of concentrated fluids, to increase the pressure thereof; pumping pure water to increase the pressure thereof, and heating the pure water to the first temperature; mixing the first concentrate and heated pure water and maintaining the mixed fluids at a sterilizing temperature for a sterilizing time to effect sterilization; delivering the sterilized and diluted concentrate fluid to a recipient; repeating the above method steps for each of the concentrated fluid components, to provide the final complex fluid for the recipient. The concentrated fluid may be preheated before being mixed with the heated water, for example by a heat exchanger by heat recovery from the sterilized fluid, which is cooled thereby.

The second fluid may be preheated by heat recovery in a heat exchanger from the sterilized fluid, which is thereby cooled, and further heated to the first temperature by a separate heating device, such as an electric heater. The heating device may be controlled by a temperature sensor positioned downstream of the maintaining step, to ensure that a sterilizing temperature is obtained.

BRIEF DESCRIPTION OF THE DRAWINGS

Further objects, advantages and features of the present invention will appear from the following detailed description of several embodiments shown in the drawings, as follows.

DETAILED DESCRIPTION

Figure 1:
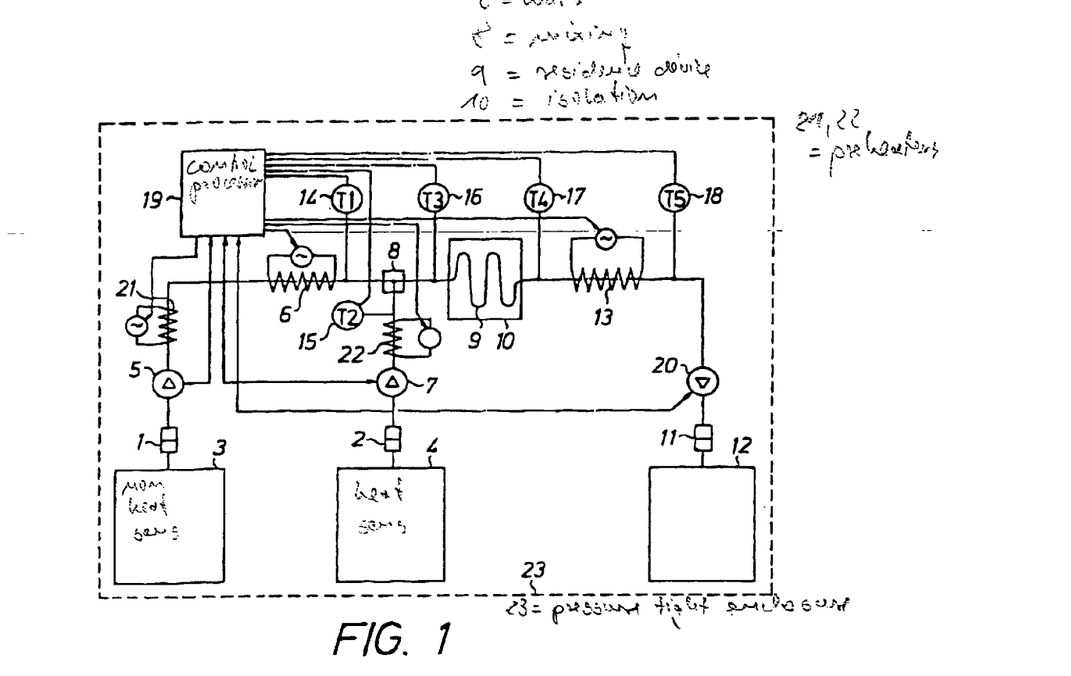
FIG. 1 is a top, elevational, schematic view of one embodiment of an apparatus for sterilizing a heat sensitive fluid according to the present invention.

The fluid to be sterilized according to the present invention comprises a first non-heat-sensitive portion and a second heat sensitive portion. According to the present invention, these two portions are delivered separately to the sterilizing device into two separate inlets 1 and 2.

With reference to FIG. 1, the first non-heat-sensitive component, which may comprise sodium chloride dissolved in water, is enclosed in a vessel 3 connected to the inlet 1. The second heat sensitive component, which may comprise glucose, is enclosed in a vessel 4 connected to the inlet 2. The fluid components are preferably provided at a temperature at which each component is relatively stable, such as room temperature.

The first fluid portion from vessel 3 provided to inlet 1 is impelled by a first pump 5 to a heater 6, in which the first fluid portion is heated to a first high temperature. The second fluid portion is impelled by a second pump 7 and mixed with the first fluid portion at a mixing point 8 disposed downstream of the heater 6. During the mixing, the second fluid portion is rapidly heated to a sterilizing temperature, while the first fluid portion is cooled to the same sterilizing temperature. The second fluid portion does not make direct contact with the heater surface and so damage is minimised.

In order to promote rapid mixing, the fluids are impelled at such conditions that turbulent flow prevails at least after the mixing point 8. In addition, flow mixing means may be arranged in the flow path, such as at the mixing point 8 or in the flow path downstream of mixing point 8. Such flow mixing means may be flanges or wings in the flow path.

The mixed fluid portions pass through a sterilizing tube section 9 which is dimensioned to provide a predetermined resident or sterilizing time period for the mixed fluids at the sterilizing temperature. The tube section may be insulated as indicated by box 10 in order to maintain the mixed fluids at the sterilizing temperature for the sterilizing time period. After the sterilizing time period, the mixed fluids are sterile, since the second fluid portion has been subjected to the sterilizing temperature during a sterilizing time period and the first fluid portion has been exposed to a still higher temperature for a still longer time period, thus being over-sterilized.

The sterilizing dose is a function of temperature and time and is defined according to the formula:

$$F_0 = \int_0^t 10^{(T-121)/10} dt$$

in which
$F_0$=the sterilization dose, in minutes
T=temperature
t=time

If the sterilizing temperature is 121° C. and the time is 20 minutes, a sterilization dose, $F_0$, of 20 minutes is obtained. If the sterilizing temperature is 141° C. and the time is 12 seconds, a sterilization dose $F_0$ of 20 minutes is also obtained. A sterilizing dose $F_0$ of 20 minutes is considered sufficient, however, in certain applications, a sterilizing dose $F_0$ of 10 minutes or even lower may be sufficient.

In the above example, the first fluid portion may comprise sodium chloride at a concentration of 150 mM, sodium lactate at a concentration of 38.8 mM, magnesium chloride at a concentration of 0.56 mM and calcium chloride at a concentration of 1.89 mM. The second fluid portion may comprise glucose at a concentration of 40%, i.e. 400 g glucose per liter of solution. The first fluid portion flow rate is 45 ml/min and the second fluid portion flow rate is 5 ml/min. The resulting mixture has the following composition: sodium chloride 135 mM, sodium lactate 35 mM, magnesium chloride 0.5 mM, calcium chloride 1.7 mM and glucose 4%. The first fluid portion is heated from 20° C. to 155° C. by the heater 6. The second fluid portion is heated from 20° C. to 141° C. during mixing, while the first fluid portion is cooled from 155° C. to 141° C. The resident or sterilizing time period is 12 seconds, resulting in a sterilizing dose, $F_0$, of 20 minutes. The resulting sterilized fluid mixture is cooled by a cooler 13 and delivered to an outlet 11 and collected in a vessel 12. A pump 20 or other device may be arranged to control the flow to the vessel 12. The sterile fluid may be used as a peritoneal dialysis solution to be delivered to the peritoneal cavity of a patient.

Other medical fluids may be produced by the device according to the present invention, such as hemodialysis solutions, infusion solutions used in hemodiafiltration or hemofiltration, replacement fluids for infusion in the blood, wound irrigation solutions, rinsing solutions, etc. Moreover, nutrition solutions often comprises amino acids, which are heat sensitive, and glucose, which is heat sensitive, and cannot be sterilized together with amino acids. Certain drugs, such as insulin, may be produced or included in a fluid administered to a patient, and the drug component may be heat sensitive. Certain medical fluids comprise peptides, proteins or fragments thereof, which normally are heat sensitive. Preservation fluids for blood component handling may also comprise heat sensitive components, at least glucose. In certain cases, glucose is replaced with or complemented with glucose polymers, di-sacharides, tri-sacharides etc. Certain carboxylic acids are heat sensitive and may be included in such fluids. Solutions comprising calcium or magnesium ions and carbonate or bicarbonate ions may precipitate upon exposure to a sterilizing temperature, and need to be sterilized with the carbonate or bicarbonate separate from the calcium or magnesium containing solution.

In order to control the above procedure, one or more temperature sensors are provided. A first temperature sensor 14 may be arranged immediately downstream of the heater 6 to determine the temperature of the first fluid portion after heating. A second temperature sensor 15 may be arranged between the second inlet 2 and the mixing point 8 to determine the temperature of the second fluid before mixing. A third temperature sensor 16 may be arranged downstream of the mixing point to determine the mixing temperature. A fourth temperature sensor may be arranged downstream of the sterilizing section 9 to determine the sterilizing temperature. A fifth temperature sensor 18 may be arranged downstream of cooler 13 to determine the temperature of the fluid delivered to vessel 12. Not all of these five temperature sensors are needed, so that one or more thereof may be excluded.

A control processor 19 may be arranged to control the sterilizing device according to the present invention. As shown in FIG. 1, the five temperature sensors are connected to the processor as well as the pumps, 5, 7 and 20, to provide measurements of the temperatures and flow rates. The pumps, 5, 7 and 20, may be volumetric pumps, also acting as flow meters. Alternatively, separate flow meters may be provided. The processor controls the heater 6 to provide the required temperature downstream of the heater, as measured by temperature sensor 14, to provide the sterilizing temperature after mixing, as measured by temperature sensors, 16 and 17. The processor calculates the residence time in the sterilizing section 9 based on the flow rates of pumps, 5 and 7, and the known volume of the sterilizing section 9. Finally, the processor may determine the obtained sterilizing dose, $F_0$.

The control processor 19 may obtain all necessary information in order to calculate the sterilizing effect from the flow rates of pumps 5 and 7 and the temperature of sensor 17.

As also shown in FIG. 1, the fluids provided to inlets 1 and 2 may be preheated by preheaters, 21 and/or 22.

Since the sterilizing apparatus shown in FIG. 1 is intended to heat the fluids to temperatures well above 100° C., it is required to keep the fluids from boiling. This may be done by enclosing the entire apparatus in an enclosure 23, as shown by broken lines in FIG. 1, and raising the pressure inside the enclosure to a pressure sufficient to prevent boiling, such as from about 3 to 6 Bar absolute pressure.

It is known that glucose decomposes when exposed to heat, and is thus a heat sensitive component of the fluid. Glucose also decomposes during storage. It is known that several factors influence the decomposition of glucose, among which are pH, temperature, time, glucose concentration and mixing with certain ionic components. Glucose decomposes into components, some of which may be more or less toxic or are able to induce toxic reactions by including precursors for such reactions. If the resulting fluid is to be used as a medical fluid for infusion into a human being or other mammal, the toxic components or precursors should be minimised.

In order to sterilise the fluid it is necessary to expose the fluid to sterilizing conditions. There are several methods available, such as heat sterilization (autoclaving), filter sterilization and other methods. The present invention is limited to heat sterilization.

During heat sterilization, it is known that decomposition of glucose can be minimised if glucose is sterilized during a short time at a high temperature. The rationale is that the decomposition reaction is less sensitive to high temperature than in the sterilizing reaction.

In order to minimise the decomposition before sterilization, it is advantageous to store the fluid at a low pH and at a high concentration, which is suggested according to the present invention. The pH may be from about 2.6 to 5.0, and preferably about 3.2. The concentration may be above 15%, or above 20%, with 40% to 50% being preferred, calculated as weight of glucose per liter solution.

The sterilization may take place during a short time and at a pH of below about 5.5 and at a final dilution concentration. It is believed that the short time is of greater importance than the other factors for avoiding decomposition into toxic components of glucose during the sterilization process.

It is also recognised that glucose may decompose into precursors for AGE (advanced glucosylation end products). When a glucose solution comprising precursors for AGE contacts proteins in the body, a non-enzymatic reaction takes place, resulting in AGE formation. The long term effect of AGE is still not well known. Gentle heat sterilization of glucose as suggested in the present invention is expected to reduce the level of glucose degradation products of the type of AGE precursors.

Figure 2:
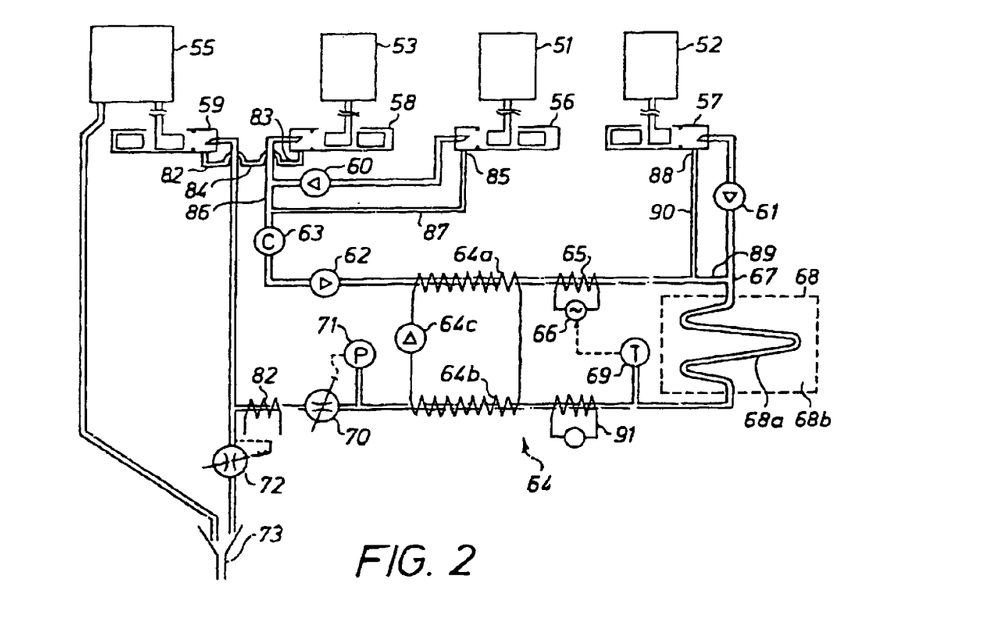
FIG. 2 is a top, elevational, schematic view of another embodiment of an apparatus according to the present invention.

An alternative embodiment of the present invention is shown in FIG. 2. In this embodiment the sterilizing device according to the present invention is integrated in a PD monitor which is arranged to provide a PD solution to a patient. The PD solution is prepared from two concentrates provided in two concentrate bags 51 and 52 and connected to concentrate input connectors 56 and 57, and a supply of pure water, for example provided from a reverse osmosis (RO) unit 53 connected to a water input connector 58 for connection to a potable water supply. The sterilized PD fluid is delivered to a PD cycler 55, which is, in turn, connected to a PD fluid output connector 59 for delivery to the patient.

Figure 4:
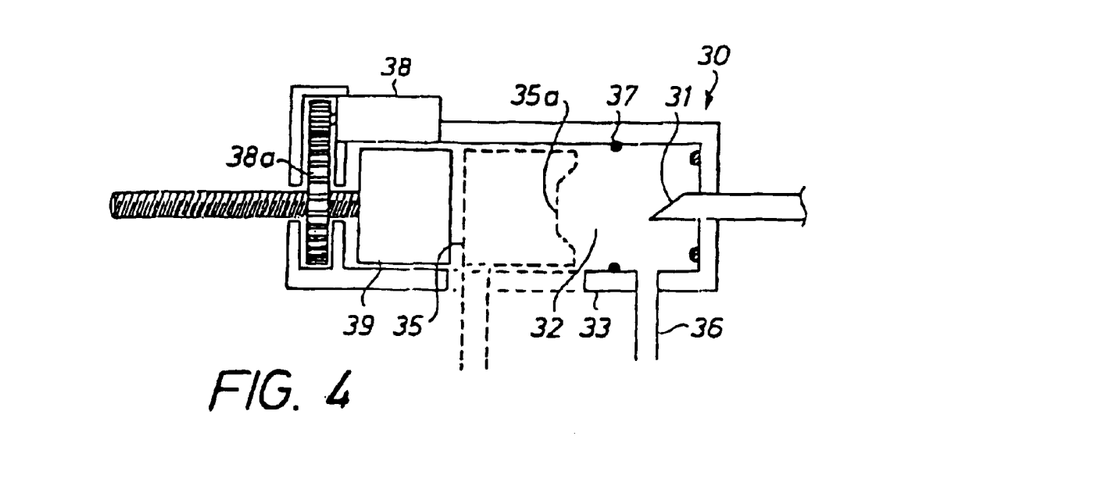
FIG. 4 is a side, elevational, cross-sectional view of a heat sterilisable connector used in the apparatus according to FIG. 2.

Each of the three input connectors and the output connector is arranged as a heat sterilisable connector device as shown in more detail in FIG. 4. Such a heat sterilisable connector device 30 is described in International Application No. WO 96/05883 and comprises a spike 31 opening into a bore 32 in a housing 33. The bore is arranged to receive a connector 35 connected to a vessel or bag, for example comprising the concentrate. The connector has a shape which is complementary to the bore, such as cylindrical, and which may be inserted into the bore to seal the bore by means of an O-ring 37. The connector is further provided with a membrane 35a which is pierceable by spike 31. The connector 35 is operable by a piston 39 to be pushed into the bore into a first position sealing the bore 32. The piston is operable by a motor 38 operating a screw and nut arrangement 38a or any other suitable driving device, like a pneumatically or hydraulically operated device.

During operation, the connector 35 is inserted in the bore 32 into co-operation with the O-ring 37. A rinsing, disinfecting and/or sterilizing fluid is circulated through the spike 31 into the bore 32 and out through a side opening 36 in the bore. The spike, bore and the membrane of the connector are thus rinsed, disinfected and/or sterilized. When the rinsing, disinfecting and/or sterilizing operation is finished, the piston 39 pushes the connector 35 further into the bore 32 so that the spike 31 penetrates the membrane 35a to thereby establish a connection between the spike and the vessel connected to the connector 35. At the same time, the connector seals off the side opening 36 and an area around the spike 31.

The connector device 30 may also be used without inserting a connector 35 by passing the piston 39 into the bore 32 into co-operation with the O-ring seal 37 to establish a flow path through spike 31 into side opening 36.

Returning now to FIG. 2, each of the inputs, 56, 57 and 58, and the output 59 is arranged as a connector device 30 of FIG. 4. Input 56 is arranged to connect a first concentrate bag 51 to a first metering pump 60 and input 57 is arranged to connect a second concentrate bag 52 to a second metering pump 61. Input 58 is connected to RO-unit 53 and a third pump 62 is arranged to pump pure water from RO-unit 53.

Pumps 62 and 60 are driven to mix the concentrate from bag 51 with pure water from RO-unit 53 to provide a desired concentration. A conductivity cell 63 may be arranged to measure the conductivity of the mixture and may control pump 60 and/or 62 to obtain the required conductivity and thus the desired concentration. Pump 62 is preferably driven to provide a constant flow of, for example, 54 ml/min and at the same time increase the pressure to from about 3 to 6 Bar absolute pressure, to avoid boiling during sterilization. The fluid provided so far is the first heat-insensitive fluid mentioned above.

The first fluid passes through a first heat exchanger 64 comprising a primary circuit 64a for heating the first fluid, for example from about 20° C. to 100° C. Then, the first fluid passes through a heater 65, such as an electric heater powered by an electric power supply 66, to heat the first fluid to a temperature of 155° C.

The second, heat sensitive, fluid from bag 52 is pumped by pump 61, at a flow rate of 6 ml/min to a mixing point 67 immediately downstream of heater 65 to mix with the first fluid. The second fluid is thus rapidly heated from room temperature to a temperature of 141° C. by being mixed with the hot first fluid, which at the same time cools down to 141° C.

Then, the mixed fluids pass through a sterilizing unit 68 comprising a tube 68a of a length suitable for providing a residence time, giving the required sterilizing time, such as 12 seconds. The tube is embedded in an insulating material 68b to minimize temperature decrease during the residence time.

Immediately downstream of the sterilizing unit 68 is a temperature sensor 69, which controls the power supply 66 so that the temperature is the desired sterilizing temperature, such as 141° C.

Pump 61 is controlled in order to deliver the heat sensitive fluid in the amount desired. For example, if the heat sensitive fluid is glucose at a concentration of 40%, the flow rate should be 6 ml/min to give a final concentration of 4% if the first flow rate is 54 ml/min. If a concentration of 1.5% is desired, the flow rate should be 2.1 ml/min and if a concentration of 2.5% should be obtained, the flow rate should be 3.6 ml/min. In each case, the temperature sensor adjusts the power supply to heat the first fluid to a suitable temperature so that the sterilizing temperature is obtained.

Downstream of the sterilizing unit 68, the now sterilized fluid enters the secondary circuit 64b of the heat exchanger 64 to rapidly decrease the temperature of the sterilized fluid, for example to 60° C. Then, the sterilized fluid passes a flow restrictor 70 to decrease the pressure to close to atmospheric pressure. Preferably, the flow restrictor 70 is controlled by a pressure sensor 71, so that the pressure before the restrictor is the desired pressure to prevent boiling, such as 6 Bar absolute pressure.

From the flow restrictor 70, the sterilized fluid is delivered to the output 59, which is connected to a PD cycler 55. A pressure relief valve 72 is arranged to connect the sterilized fluid to a waste 73 if the pressure of the fluid exceeds a predetermined value, such as 150 mmHg above atmospheric pressure.

The PD cycler may be of the type described in International Application No. WO 95/20985, comprising a pressure chamber. A disposable line set is connected between the outlet connector and the patient and comprises a heater bag and a drain bag, a drain line and a supply line. The heater bag and a drain bag are arranged on a weighing device, such as a pair of scales. Four valves in a valve unit are arranged to operate on the drain and supply lines. Finally, the line set comprises a PD connector for connection to a catheter into the peritoneal cavity of the patient. The PD fluid from outlet 59 is supplied to the heater bag by means of the valve unit until the scales indicate that the heater bag has been filled to a predetermined volume, such as 3 liters. Then the patient is drained by exposing the pressure chamber to a subpressure to withdraw fluid in the peritoneal cavity of the patient out through the open valve unit into the drain bag. The combined weight of heater bag and drain bag is weighed and the drain phase is terminated when it is determined that the drain flow rate is below a predetermined limit or a drain time has elapsed. The drain flow rate is determined by means of the weighing device. Then, the pressure chamber is exposed to an overpressure and the valve unit is opened to allow the fresh sterilized PD fluid to flow into the peritoneal cavity of the patient. The flow rate and the delivered fluid volume is monitored, and the fill phase is terminated when a desired fill volume has been delivered. The temperature of the heater bag is controlled by a heating device and temperature sensor so that the fluid delivered has a temperature of about 37° C. Finally, the drain bag is emptied to the waste by opening the valve unit and exposing the pressure chamber to an overpressure.

When the patient has been exposed to a fluid exchange as described above, the PD fluid is left in the peritoneal cavity for a dwell time until the next exchange cycle. During the dwell time period, the sterilizing device provides new sterile fluid to the heater bag. It takes about 33 minutes to produce a fill volume of 2 liters if sterile fluid is produced at 60 ml/min.

It may be desirable to include a cooler 82 after the flow restrictor 70 in order to further decrease the temperature before delivering the fluid to the heater bag. The cooler may be a Peltier cooler or a heat exchanger of conventional design, using cold water or a cooling medium as heat energy absorption medium. A cooler 91, such as a Peltier cooler, may alternatively or additionally be placed after residence device 68 and before heat exchanger 64, in order to rapidly cool the heat sensitive mixture to a safe temperature, such as from 141° C. to 120° C. In this manner, the heat sensitive component is rapidly heated from room temperature to sterilization temperature of 141° C. at mixing point 67, is maintained at the sterilizing temperature during 12 seconds by residence device 68 and is then rapidly cooled to 120° C. by Peltier cooler 91 and then further cooled to room temperature in the slightly slower heat exchanger 64

The sterilizing device needs to be disinfected at suitable intervals, for example once per day or once per week. For that purpose, the side openings of the connector devices, 56, 57, 58 and 59, are used. The side opening 83 of RO inlet 58 is connected to the side opening 82 of outlet 59 through a line 84. The side opening 85 of first inlet 56 is connected to the flow line 86 between RO inlet 58 and the pump 62 through a line 87. The side opening 88 of second inlet 57 is connected to the line 89 between heater 65 and sterilizing unit 68 through a line 90.

During disinfection, the sterilizing device is filled with pure water obtained from the RO-unit. Then, connectors, 57, 58 and 59, are disconnected from the respective sources and the piston is arranged in the position in conjunction with the O-ring, in order to seal the bore 32 of the connector opening, (see FIG. 4).

Thus, the RO-inlet connector 58 and the outlet connector 59 are connected through line 84 and side openings 82 and 83. The second inlet connector 57 is in the same position so that a circulating path is obtained by means of pump 61, line segment 89, line 90, side opening 88 and inlet 57. A disinfecting solution is provided in a vessel connected to the first inlet 56. The disinfecting fluid may be sodium carbonate, citric acid or any other known disinfection fluid. Pumps 62 and 61 are operated to circulate the water in the circuits. Finally, pump 60 is operated to infuse disinfection fluid into the water until a sufficient disinfectant concentration has been obtained. The surplus water is rejected by means of relief valve 72 to the waste 73. Pump 62 circulates the disinfection fluid through the complete sterilization device and the outlet 59 is connected to the inlet 58 through line 84 to complete the circuit. The disinfection fluid may be left in the machine until the next use. Before the next use, the machine is rinsed with pure water through inlet 58 from the source of RO-water.

Descaling with citric acid or other descaling agent is performed in the same manner.

In order to avoid dripping from the connectors, the inlet connectors, 56, 57 and 58, and the outlet connector 59 are positioned at the highest position of the flow path and at the same level.

The machine may be emptied by opening all inlets, 56, 57 and 58, and the outlet 59 and by opening the relief valve 72, which is positioned at the lowest point of the flow path, and by allowing air to enter all lines and devices.

During chemical disinfection and/or descaling, the heater 65 may be turned off or adjusted to heat the fluid to a low temperature. The flow restrictor 70 may be opened.

In heat sterilization, the fluid in the entire circuit is heated to 121° C. and circulated for at least 20 minutes to obtain sterilization of the entire circuit. In this case, pressure relief valve 72 is operated to permit a pressure of 2 Bar, thereby preventing boiling of the water in the circuit at 121° C.

The same or a similar procedure may be used for sterilizing the flow path of the sterilizing device. The fluid circuit is arranged for a treatment with all connectors inserted in respective bore 32 in the non-engaged position. The circuit is filled with water, which is circulated by pump 62. Flow restrictor 70 is opened and relief valve 72 is adjusted to a pressure of from about 2 to 3 Bar absolute pressure. First inlet connector 56 is operated to connect the vessel 51 to the circuit. Then, pump 60 is operated to introduce some fluid (electrolyte fluid) in the circuit until the pressure reaches about 2 to 3 Bar absolute pressure. Since the fluid circuit is relatively non-compliant, the volume of fluid introduced is very small. Then, the heater is activated to heat the water present in the circuit to a temperature of 121° C. and the circulation continues for 20 minutes or longer, until sterilization is obtained. Pump 61 is operated simultaneously to sterilise the circuit comprising inlet connector 57.

After sterilization has been obtained, RO inlet 58 is activated to connect RO-unit 53 to the circuit and at the same time disconnect bypass line 84. Pump 60 is stopped, and heater 65 is activated. Flow restrictor 70 is activated and pressure relief valve 72 is adjusted to the normal value of 150 mmHg overpressure. Thus, sterile water is produced and delivered to the waste 73 by means of relief valve 72. Then, the second inlet is activated to connect vessel 52 and pumps, 60 and 61, are operated to provide a PD fluid. When stable conditions are obtained, the outlet 59 is activated to deliver sterilized fluid to the heater bag.

During the drain and fill phases of the PD cycler, the sterilizing device may continue to produce PD fluid. However, since the valve unit is closed, the PD fluid produced is directed to the waste 73 by means of relief valve 72. Since the drain and fill phases may last up to 20 minutes or more, a considerable amount of PD fluid is wasted. To minimise such waste, pumps 60 and 61 may be stopped during the periods when the heater bag is not being filled, and the sterilizing device is only producing and wasting sterile water.

The first and/or second concentrates may comprise the same substances or components as mentioned above, however, with the contents of the first vessel 51 concentrated by omitting some of the water. The contents of the first vessel may be concentrated, for example, about 30 to 40 times. In an alternative embodiment, the PD fluid is intended to comprise bicarbonate instead of or in addition to lactate. Calcium cannot be included in the same vessel as bicarbonate, because of the risk of precipitation of calcium carbonate. In that case, the calcium chloride may be included in the second vessel 52 in a suitable concentration. The calcium concentration will then be proportional to the glucose concentration, which may result in a calcium neutral PD fluid. Another advantage of including the calcium ions in the second vessel is that scaling of the pipe system is avoided before the mixing point 67, and the requirement for descaling would decrease.

Figure 3:
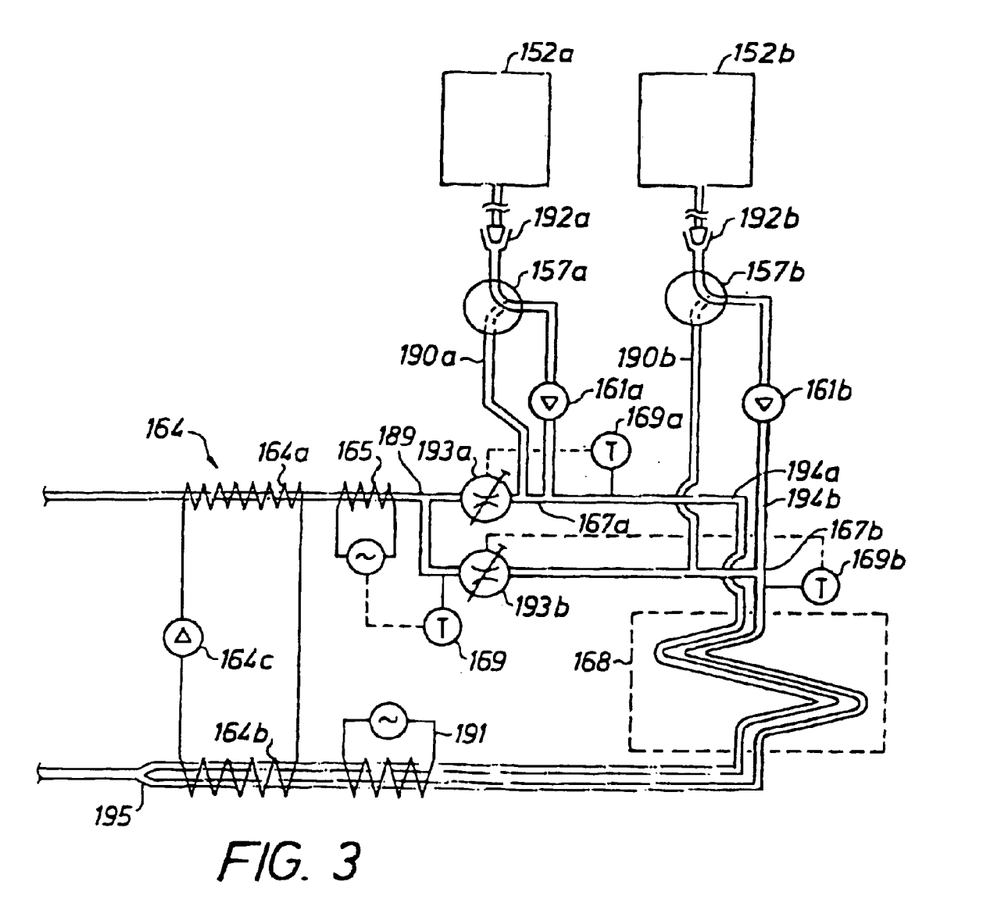
FIG. 3 is a top, elevational schematic view of a portion of yet another embodiment of an apparatus according to the present invention.

Each of the sterilizable connectors may be replaced by a conventional connector device and a three way valve of conventional type, as shown in more detail in FIG. 3, which shows an alternative embodiment of the present invention.

FIG. 3 shows an alternative design of a mixing system delivering the mixed fluids in parallel through the residence device. FIG. 3 shows only the right-hand portion of FIG. 2 to the right of pump 62 and pressure sensor 70. The left-hand portion may be identical to the embodiment shown in FIG. 2. The same components as in FIG. 2 have received the same reference numerals, but 100 is added to the reference numbers. Thus, there is shown a heat exchanger 164 comprising a primary circuit 164a and a secondary circuit 164b and a pump device 164c. An electrolyte solution or pure water is conducted through line 189 through heat exchanger primary circuit 164a and a second heater 165, for example an electric heater controlled by a temperature sensor 169.

A first bag 152a comprising a heat sensitive first component such as glucose is connected by means of a connector 192a to a three-way valve 157a. The first component passes from the three-way valve 157a to a pump 161a and further to a mixing point 167a, in which the first component is heated to 141° C. by mixture with a heated electrolyte component, having a temperature sufficient for promoting such heating by mixing, the temperature being, for example, 155° C. The mixing temperature is controlled by a temperature sensor 169a, which operates a throttle valve 193a disposed before the mixing point 167a. By throttling the valve 193a, a sufficient flow rate for obtaining said temperature is adjusted.

A second bag 152b comprising a heat sensitive second component, such as amino acids, is connected by means of a connector 192b to a three-way valve 157b. The second component passes from the three-way valve 157b to a pump 161b and further to a mixing point 167b, in which the second component is heated to 141° C. by mixture with a heated electrolyte component, having a temperature sufficient for promoting such heating by mixing, the temperature being, for example, 155° C. The mixing temperature is controlled by a temperature sensor 169b, which operates a throttle valve 193b arranged before the mixing point 167b. By throttling the valve 193b, a sufficient flow rate for obtaining said temperature is adjusted.

The two heat sensitive components heated to sterilizing temperature by mixture with the electrolyte component are handled in parallel in two separate lines, 194a and 194b, which pass in parallel through the residence device 168, the pre-cooler 191, if present, and to heat exchanger secondary circuit 164b. After cooling in the heat exchanger, the two fluids are mixed in a Y-connector 195 before entering the restriction device 70 (see FIG. 2). The bags 152a and 152b are weighed and when a sufficient amount of fluid has been taken out from each bag, valve 157a and/or valve 157b are switched to stop the flow of first and/or second components from bags 152a and 152b, respectively.

During sterilization, the three-way valves, 157a and 157b, are connected according to the broken lines in FIG. 3, in order to pass fluid, by means of pumps, 161a and 161b, in the fluid lines to and from the three-way valves, 157a and 157b, through lines 190a and 190b.

It can be seen that more than two heat sensitive components may be handled in parallel by adding further bags 152 and further lines 194. The same procedure may be adopted for components which are less heat sensitive, to obtain a simple system, whereby the electrolyte component may be replaced with pure water, and thus, the electrolytes may be added one by one, or several at a time.

Figure 5:
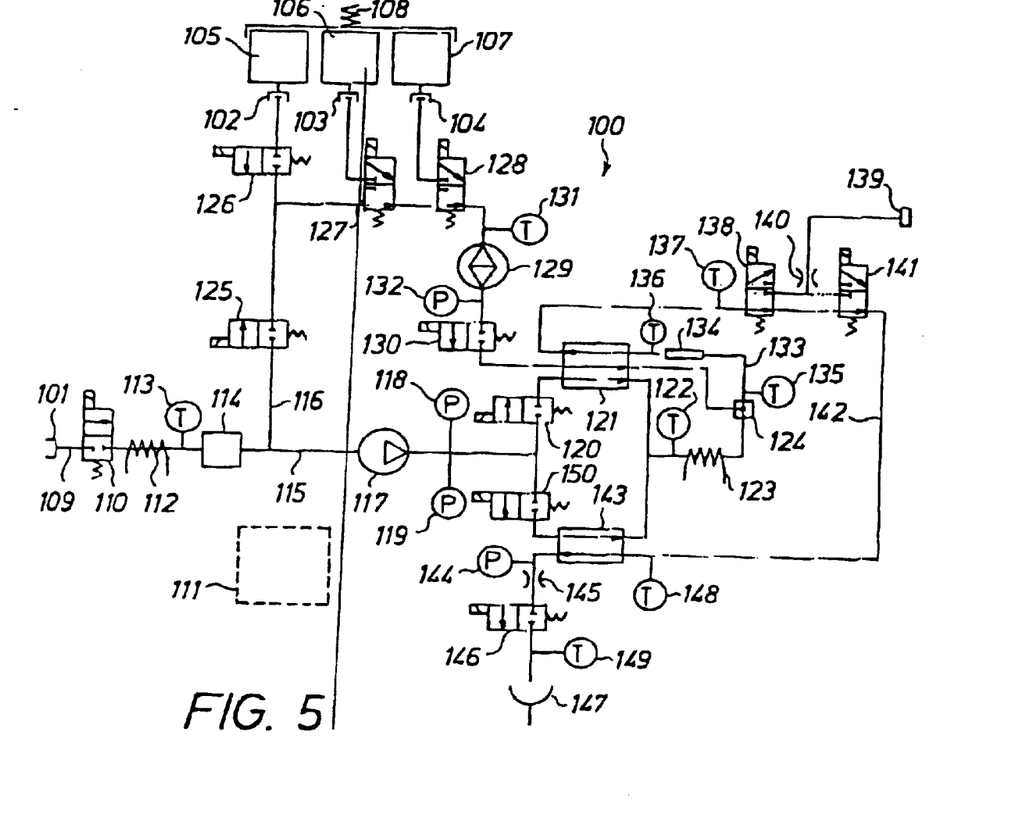
FIG. 5 is a top, elevational, schematic view of yet another embodiment of the apparatus according to the present invention.

A further alternative embodiment of the present invention is shown in FIG. 5. From the left, the device 100 comprises a connector 101 for connection to a source of pure water, such as an RO-unit (not shown). The device further comprises three concentrate connectors, 102, 103 and 104, which may be integrated into a single connector device. Each of the connectors, 102, 103 and 104, connects to a vessel or bag comprising a concentrate, such as a first bag 105 comprising a concentrated bicarbonate solution, a second bag 106 comprising electrolytes, such as sodium chloride, magnesium chloride, calcium chloride, and sodium lactate, at a predetermined pH, and a third bag 107 comprising glucose at a concentration of 50%. The bags include the components necessary for the final solution, as discussed in more detail below. The components are divided into separate bags because they cannot be stored together, or they cannot be sterilized together, or for other reasons.

Alternatively, one or more of the vessels or bags, 105, 106 and 107, may comprise a powder instead of a solution, in which case appropriate dissolution means may be provided.

Conveniently, the bags, 105, 106 and 107, are combined into a single assembly. The combined assembly of bags is attached to a weighing device 108, so that the weight of the assembly is monitored. The connectors, 102, 103 and 104, are attached to the ends of flexible tubes of PVC or other suitable pliable material, so that the connectors and tubes do not significantly influence the weight of the assembly. The RO inlet connector 101 is connected to a line system including a first inlet line 109. Inlet line 109 is provided with a inlet valve 110, to isolate the device 100, if required. Inlet valve 110 is normally closed, but is opened upon activation by a control device 111, shown by broken lines. The control device may be a computer or microprocessor or any other control device. Normally, it is the control computer of the complete device.

Inlet line 109 further comprises a heater 112 and a temperature sensor 113, which operate together to adjust the temperature of incoming pure water to a predetermined temperature of, e.g., 25° C., in order to make the device independent of incoming water temperature.

Inlet line 109 further comprises a flow meter 114 for measuring the complete inlet flow through inlet connector 101, for a purpose to be described later.

Downstream of flow meter 114, inlet line 109 is divided into water line 115 and concentrate line 116. Water line 115 comprises a first pump 117 for increasing the pressure of the water in water line 115 downstream of the pump to a pressure of from about 2 to 6 Bar absolute pressure. The pressure is measured by a first pressure sensor 118 and monitored by a second pressure sensor 119. The first pressure sensor 118 is connected to the control system of computer 111, while the second pressure sensor 119 is connected to a parallel supervising system for ensuring the safety of the system. Several of the sensors are duplicated in this manner to provide independent data to the supervisory system or processor, even if not explicitly indicated in the drawings.

Water line 115 further comprises a valve 120 and a primary circuit of a heat exchanger 121. In the heat exchanger, the water in water line 115 is heated from about 25° C. to about 131° C. in heat exchanger 121, at a flow of about 120 ml/min. The temperature of the heated water is monitored by temperature sensor 122. Finally, water line 115 comprises a second heater 123, for heating the water to a still higher temperature, such as about 145° C. The hot water is delivered to a mixing point 124.

In concentrate line 116, there is a valve 125 for connecting the normally closed concentrate line 116 to water line 115. Further downstream, concentrate line 116 comprises three concentrate valves, 126, 127 and 128, and a reversible second pump 129. The second pump 129 is arranged to withdraw concentrate solutions or fluids from any one of concentrate bags, 105, 106 or 107, depending on the positions of the valves, 126, 127 and 128. The second pump 129 further increases the pressure of the fluid in concentrate line 116 to a pressure of about 2 to 6 Bar absolute pressure.

Downstream of second pump 129 is arranged a valve 130, and, the concentrate fluid is delivered therefrom to a second primary circuit of heat exchanger 121 in order to preheat the concentrate solution from e.g. room temperature to about 131° C. From heat exchanger 121, the concentrate solution is delivered to mixing point 124.

Upstream of the second pump 129 is disposed a temperature sensor 131 for measuring the temperature of the incoming concentrate fluid, and downstream of the second pump is disposed a pressure sensor 132 for measuring that sufficient pressure has been obtained. As indicated above, these sensors may be duplicated for supervisory purposes.

In mixing point 124, the two fluid lines 115 and 116 are joined so that the heated water in line 115 is mixed with preheated concentrate in line 116, and the mixture is transported in mixed fluid line 133. Mixed fluid line 133 comprises a residence device 134, normally being a length of tube of a length to produce a predetermined residence time at a predetermined rate of flow to effect sterilization of the fluid in the residence device 134. The residence device 134 is preceded by a temperature sensor 135 and followed by a temperature sensor 136. These temperature sensors control the heater 123 to ensure that sterilizing conditions are obtained in the residence device 134, such as a minimum temperature of 141° C. for 12 seconds.

From the residence device 134, the sterilized and mixed fluid is passed to the secondary circuit of heat exchanger 121, at a temperature of approximately 141° C. The sterilized fluid is rapidly cooled to about 37° C.

Downstream of the heat exchanger, mixed fluid line 133 comprises sterilized fluid at a temperature suitable to be delivered to a patient or a storage bag. The temperature is monitored by a temperature sensor 137. Finally, a valve 138, when activated, directs the fluid to an outlet connector 139, by means of a restrictor device 140, for lowering the pressure to atmospheric pressure.

The restrictor device may be a small hole in a piece of metal, the hole being dimensioned to reduce the pressure from 6 Bar to 1 Bar at the desired flow rate of, for example, 140 ml/min. An alternative design would be to use a controllable throttle valve, which is controlled by the processor dependent upon pressure sensor readings. A third alternative would be to use a throttle device or the pressure relief type, which adjust the differential pressure over the throttle device to a predetermined pressure drop, for example, of about 5 Bar. A fourth alternative would be to use a throttle device controlled to deliver fluid at an output pressure of no more than a predetermined safe pressure of, for example, 1.25 Bar, in which case the pumps are operated to ensure that the pressure before the throttle device is sufficiently high, for example about 6 Bar.

It is noted that the on-line autoclave as described is always operated at a predetermined minimal flow rate of not less than a predetermined flow rate, for example 120 ml/min, in order to ensure that the autoclave is maintained sterile. As soon as the flow rate drops below the predetermined minimum flow rate, the sterility conditions may be hampered or the autoclave may not be controlled to operate at proper temperatures. The autoclave may be designed to operate different flow rates above the minimum flow rate. In order to always maintain a minimal flow rate, any excess fluid produced is sacrificed to the waste.

If the mixed and sterilized fluid cannot be delivered out by means of the output connector 139, a valve 141 is activated to deliver the fluid to a sump or waste through a waste line 142. Waste line 142 further comprises a primary circuit of a second heat exchanger 143, a pressure sensor 144, a restrictor device 145 and a valve 146 until the fluid is delivered to the waste 147. A temperature sensor 148 arranged upstream of heat exchanger 143, and another temperature sensor 149 arranged downstream of valve 146, are used to measure the temperatures of the waste fluid.

The device according to FIG. 5 may be operated in different modes. One mode of operation will be described below, namely sequential delivery of the components of the final fluid. It is, however, understood that the device may operate as described in connection with FIG. 2 as well.

In the sequential operation mode, water is first delivered in inlet line 109 at a constant rate of 120 ml/min from inlet connector 101, by means of flow meter 114, in which the flow rate is monitored, and through water line 115 and first pump 117 to raise the pressure so that the boiling temperature of the fluid is above the temperature anywhere in the circuit. If the maximum temperature is about 150° C., the pressure should be above 4.8 Bar or preferably about 6 Bar absolute pressure. The exact pressure is dependent on the adjustment and operation of restriction device 140. The water further passes the mixing point 124 and enters the mixed fluid line 133 and reaches valve 138, which directs the flow to waste line 142, by means of valve 141, and further to the sump. The outlet connector 139 is connected to a recipient, normally a bag, such as a heater bag described below.

When all conditions are checked, and the device delivers sterilized water, valve 138 is switched to direct the sterilized water to the outlet connector 139 by means of restrictor 140.

Substantially at the same time, or shortly thereafter, valve 127 in concentrate line 116 is opened and concentrate pump 129 is activated, with valve 130 in an open condition, to pump concentrate fluid from electrolyte bag 106, by means of heat exchanger 121 to mixing point 124. The concentrate pump 130 is operated to provide a flow rate of approximately 20 ml/min. At the same time, the weight of the concentrate assembly is monitored by weighing device 108. If the intention is to provide 1 liter of final solution and the concentrate fluid in bag 106 has a concentration of 1:40, the flow is continued for about 1 minute and 15 seconds, until the weighing device indicates that a volume of 25 ml has left the bag 106, whereby 25 ml is the amount required from concentrate bag in 1 liter of final fluid (1:40).

Then, valve 127 is switched off and valve 125 is opened for a short time, such as 15 seconds, to rinse the concentrate line 116.

For including the second concentrate, which may be glucose, bag 107 is connected to the concentrate pump by closing valve 125 and opening valve 128. If the glucose concentrate fluid has a concentration of 50%, the concentrate pump is driven 1 minute per percent concentration to be required in the final fluid at 20 ml/min. If 4% is required, which is the maximum contemplated for a PD fluid, the glucose concentrate is dosed in 4 minutes.

After this step, the concentrate line 116 is again rinsed with water, for example for 15 seconds.

Thereafter, the bicarbonate bag 105 is connected. The bicarbonate is normally stored at a concentration of about 1000 mmol/l. First, valve 125 is closed and valve 126 is opened so that concentrate pump 130 pumps bicarbonate fluid out of bag 105. The flow rate may be the same, 20 ml/min, and the mixing and sterilization of bicarbonate fluid is discontinued when the weighing device determines that the required quantity has been removed from bag 105. If the final solution should contain 15 mmol/l, the concentrate pump is operated for 45 seconds to take 15 ml of concentrated bicarbonate solution out of bag 105.

Finally, the concentrate line is rinsed once again and water is delivered to the outlet connector, until the final volume of fluid has been delivered to the bag connected at the outlet connector, which is determined by flow meter 114 in combination with the weight losses measured by weighing device 108 and calculated into volumes by computer 111, taking into account the different densities of the concentrate fluids.

This final filling of water also means that the mix of fluid in the bag connected to the outlet connector is agitated and mixed thoroughly.

During the complete sterilization process described above, valves 138 and 141 are maintained in the same position directing all fluid to the outlet connector 139. Thus, all fluid produced is delivered to the receiver, thereby minimising the time required for preparation of the complete fluid.

In the example above, 1 liter of final solution has been prepared, but in PD it is more normal that 2 liters are generated each time, or any other volume as required by the user.

It is contemplated that the concentrate fluid bags may include concentrate fluid required for a final fluid volume of about 12 to 25 liters or more, if required. Then, the above sequence is repeated for each batch of 2 liters to prepare.

In certain applications for PD, bicarbonate is not used, but lactate is used as the sole buffer. In that case, the third bag in the concentrate assembly is unnecessary, and only two bags may be used. In that case, valve 126 is always closed.

To prepare one batch of 1 liter (1.5% glucose concentration), takes about 7 minutes and 45 seconds, supposing that the RO unit delivers pure water at 120 ml/min and 25 ml electrolytes, 15 ml bicarbonate and 30 ml glucose are used. Thus, the waiting time between each PD exchange of about 2 liters has to be more than 15.5 minutes. This might be limiting in some circumstances as appears from an explanation of the drain and fill phases of a PD treatment below.

Figure 6:
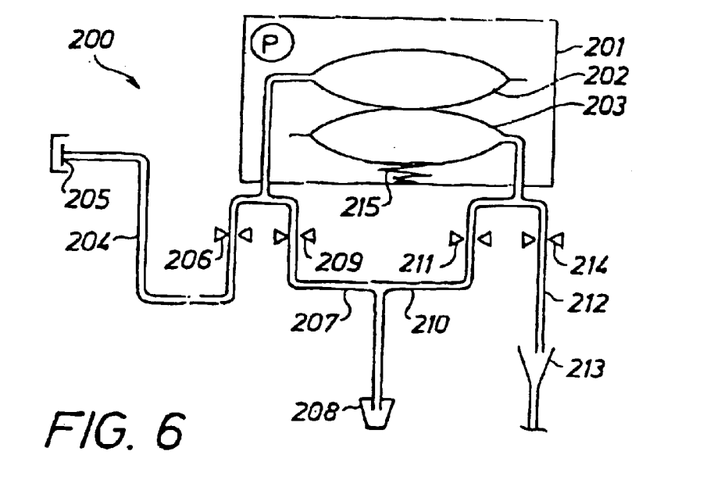
FIG. 6 is a side, elevational, schematic view of one embodiment of a cycler which may be connected to the apparatus according to FIGS. 2 or 4.

In FIG. 6 is schematically shown a PD cycler 200 intended to be used in the present invention. The PD cycler comprises a pressure chamber 201 enclosing a heater bag 202 and a waste bag 203. The heater bag 202 is connected to the outlet connector 139 of fluid sterilization device 100 of FIG. 5 for receiving a fresh sterilized fluid for introduction into heater bag 202. Heater bag 202 is connected with connector 139 by means of a first tube 204 ending with a connector 205 mating with connector 139 and comprising a valve 206. A second tube 207 connects heater bag 202 with a connector 208 to a patient (not shown) and the second tube 207 is controlled by a second valve 209. A third tube 210 connects the patient connector 208 to the drain bag 203 by means of a third valve 211. Finally, a fourth tube 212 connects drain bag 203 with a waste line 213 by means of a valve 214. Heater bag 202 and drain bag 203 rest on scales 215 which monitor the combined weight of the two bags.

Figure 7:
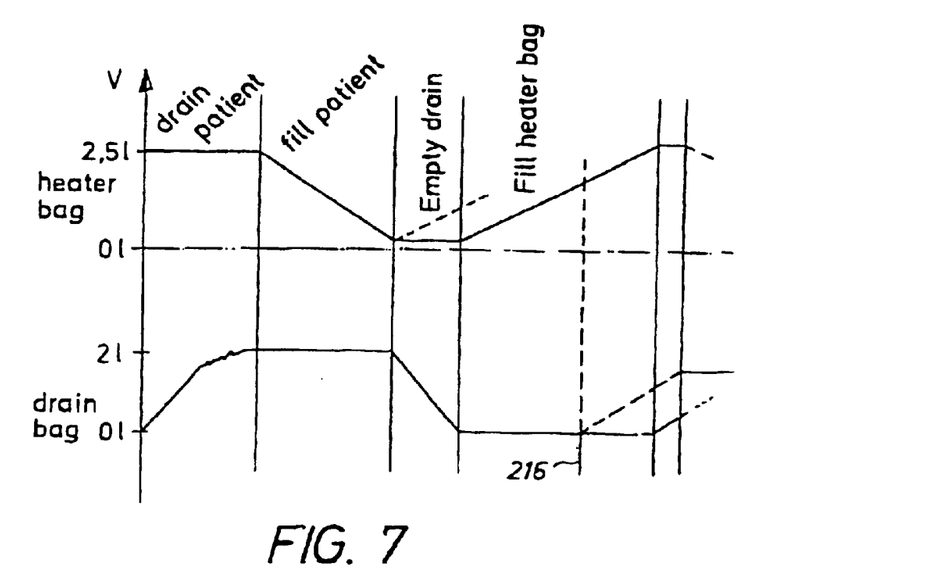
FIG. 7 is a graphical representation of a time diagram of the fluid flows in the cycler according to FIG. 6.

The operation of the PD cycler as schematically disclosed in FIG. 6, appears from the diagram of FIG. 7. The diagram indicates the fluid volumes of the heater bag and drain bag during the different phases.

After priming, which is more fully described below, the first phase of the treatment is a drain phase, at the start of which the heater bag is full of fluid, normally about 2.4 liters, and the drain bag is empty. The patient is connected and the third valve 211 is opened and a subpressure is exerted in pressure chamber 201. Fluid is withdrawn from the patient into drain bag 203 at a flow rate depending on the patient and the subpressure, normally from about 150 to 300 ml/min. When the peritoneal cavity of the patient is almost empty, which may be indicated by a decrease of the drain flow as measured by the scales 215, the drain phase is terminated. The drain phase is normally from about 7 to 10 minutes.

The second phase is a fill phase, in which the peritoneal cavity of the patient is filled with fresh fluid contained in heater bag 202. An overpressure is exerted in pressure chamber 201 and valve 209 is opened, while the other valves are closed. The fill flow rate depends on the patient and the overpressure and may be about 150 ml/min. The fill phase is normally from about 10 to 15 minutes.

The third phase is the empty drain bag phase, in which an overpressure is exerted in the pressure chamber 201 and valve 214 is open. The fluid in the drain bag is directed to a waste line 213. The volumes are always monitored by the scales 215. The third phase may be about 2 minutes, since a high overpressure may be used and the flow restriction is minimal.

The fourth phase is heater bag fill with valve 206 open. In this case, normally a subpressure is exerted in the pressure chamber 201. Fluid is received from the sterilizing device 100 connected to connector 205 at a flow rate of about 120 ml/min. The fourth phase is normally from about 15 to 17 minutes.

Thus, a complete cycle is from about 34 to 44 minutes. During a night treatment of 8 hours, it is possible to exchange from about 22 to 28liters , in batches of 2 liters.

If it is desired to increase the fluid volume further, the times in the different phases have to be shortened. It is noted that the heater bag fill time of from bout 15 to 17 minutes could be shortened by increasing the flow rate of fluid from sterilizer 100. However, increasing the flow rate means considerable cost increases.

Instead it is noted that the flow rate of the fluid delivered from sterilizer 100 is monitored by the sterilizer by flow meter 114 and weighing device 108. Thus, it is possible to fill the heater bag during (part of) the drain cycle as indicated by the broken line 216 in FIG. 7. This is done by opening valve 211 during the heater bag fill phase, before the heater bag fill phase is terminated, such as 10 minutes in advance. If the drain phase is terminated before the heater bag is filled, the drain phase has to be continued until the heater bag filling is completed. However, it is no drawback to continue the drain phase longer, since that only results in some further fluid being drained, which normally is an advantage. Since the flow from the sterilizer is known, the PD cycler still has full control of the flow by using the reading from the scales and subtracting the inflow from the sterilizer. In this way, almost the complete drain phase can be saved in the cycle time, i.e. up to about 10 minutes.

Another way of saving time is to fill the heater bag during the empty drain bag phase. It is recognised that the pressure chamber needs to have an overpressure to empty the drain bag. However, the sterilizing device is able to deliver sterilized fluid under a slight overpressure. Thus, if valve 214 is open to pass fluid to the waste and valve 206 is open to allow fluid to enter the heater bag, and if there is an overpressure inside the pressure chamber, the heater bag may be filled during the empty drain phase. Moreover, the pressure does not need to be reversed during the rest of the heater bag fill cycle, which normally is considerably longer than the empty drain bag phase. In this operation mode, it is still possible to keep accurate control over the ultrafiltration, since the volume of fluid drained from the patient and the volume of fluid filled into the patient are under full control of the mass balance device 215.

Figure 8:
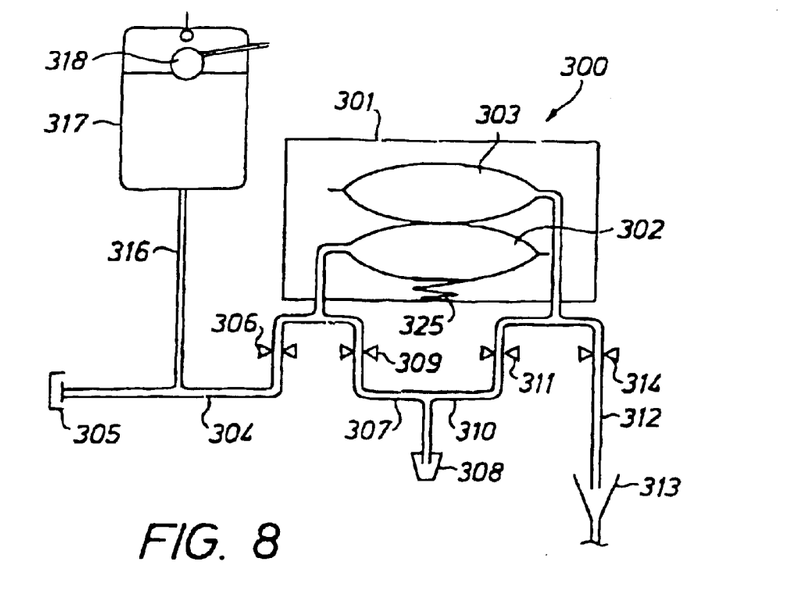
FIG. 8 is a side, elevational, schematic view of another embodiment of a cycler for use in connection with the apparatus of the present invention.

If the cycle time needs to be further shortened, that is possible by the addition of a storage bag in the line set as indicated in FIG. 8. It is noted that the sterilizer has to direct the sterilized fluid to the waste 147 during the second phase filling the patient, when valve 206 is closed, as well under the third phase emptying the drain bag.

In FIG. 8, the same components as in FIG. 6 have received the same reference numeral starting with 3 instead of 2. The inlet tube 304 is provided with a branch line 316 ending in a storage bag 317. When valve 306 is closed during the first, second and third phase, the sterilizer 100 delivers PD solution into storage bag 317 through tube 316. The heater bag 302 may then be filled much faster from the storage bag 317 compared to the embodiment of FIG. 6. Thus, the heater bag fill phase may be reduced to about 2 minutes or less. The efficiency of the complete device becomes dependent only on the cycler and its capacity to drain and fill the patient. The surplus time is merely 4 minutes, 2 minutes for emptying of the drain bag and 2 minutes for filling the heater bag. The procedure has to be controlled if the sterilizer is operated in the sequential mode as described in connection with FIG. 5, since the filling of heater bag has to start only when the concentrations are correct in storage bag 317, i.e. after the completion of a complete fill cycle from the sterilizer.

The storage bag may also be used as an entry point for addition of medicaments or other additions, like insulin, antibiotic drugs, potassium chloride etc.

It is recognised that the PD solution produced according to the sterilizer in FIG. 5 will produce sterile bicarbonate fluid and enter it in the storage bag 317, and then produce sterile glucose solution and subsequently enter that in the storage bag 317. Since the glucose fluid has a low pH, some of the bicarbonate will react and form carbon dioxide, which may be released as a gas. Thus, storage bag 317 is provided with a valve and tube arrangement 318 to indicate when there is surplus gas in the storage bag 317 and expel it to the atmosphere. Another means for doing the same thing would be to include a sterile filter or hydrophobic filter at the top of storage bag 317. The gas may be expelled in a time interval when outlet valves 138 and 140 are opened (the position shown in FIG. 5) and pressure chamber 301 has an overpressure and valve 306 is open to exert an overpressure into storage bag 317 and expel gas therein.

In the above example indicated in connection with FIG. 5, the bicarbonate concentrate was sterilized at a concentration of about 140 mmol/liter (1000×20/140). However, there is a risk that carbon dioxide is formed during heat sterilization at such a concentration, and thus, the concentrate pump may be operated at a lower speed during sterilization of bicarbonate fluid.

In FIG. 5, the concentrate fluid is preheated to quite a high temperature. This is performed in an efficient heat exchanger 121 in which the heating fluid is the final sterilized fluid in the secondary circuit of the heat exchanger. Thus, the heat exchanger cannot have any point with higher temperature than the sterilizing temperature, and decomposition of the heat sensitive component is minimised. The further heating to the final sterilization temperature, i.e. from about 131° C. to about 141° C., takes place by the method of mixing with a fluid having a slightly higher temperature. Thus, the heat sensitive fluid component is never exposed to harsh conditions, such as hot points having excessively high temperatures, as may appear in an electric heater 123. Thus, favorable conditions for less formation of degradation products are obtained. The temperature difference between the primary and secondary circuits of the heat exchanger is about 10° C., which is possible to obtain without excessive long residence times in the heat exchanger.

In FIG. 5, there is a circuit not previously described for sterilizing the equipment before use. In water line 115, a parallel circuit to valve 120 and heat exchanger 121 is arranged comprising valve 150 and the primary circuit of heat exchanger 143. When heat disinfection of the complete sterilizer 100 is to be performed before a treatment, valve 120 is closed, valve 150 is opened and heater 123 is operated. The water passes from pump 117 by means of valve 150 to heat exchanger 143 and further to heater 123 to be heated to a temperature of, for example, 141° C. The hot water passes heat exchanger 121 but is not cooled appreciably since the primary circuit of exchanger 121 is disconnected and has no flow. The hot water after heat exchanger 121 passes through line 133 and by means of valves 138 and 141 to heat exchanger 143 to give off its heat to the water passing at the primary side thereof. Finally, the water is discharged to the waste by means of restrictor device, 145, which lowers the pressure from about 2 to 6 Bar to atmospheric pressure.

Thus, the on-line autoclave is self-sterilized and is ready for producing PD fluids. The self-sterilizing step may be performed in about 30 minutes and is initiated under program control to take place shortly before the start of a PD treatment, which is scheduled in advance by a patient. When the self-sterilization process is ready, the machine awaits the arrival of the patient, which connects a disposable set, such as set 200 or 300, to the outlet connector 139. Then, the device produces a quantity of sterile treatment fluid into the heater bag. However, before the patient is connected to connector 208, the tubes should be filled with fluid to displace the air therein. This is performed by attaching the connector 208 to a hook or attachment device on the cycler at approximately the same level as the heater bag. Then, valve 209 is opened to allow fluid to flow through tube 207 to patient connector 208. The connector 208 is then ready for connection to the patient.

It is appreciated that the priming procedure described above takes about 20 minutes, since the heater bag must be filled with 2 liters of solution. If this time is too long for the patient to wait, it is possible to perform a partial fill of the heater bag with, for example, 5 dl solution produced in 4 minutes, and use this volume of fluid to prime the tubes and displace the air. Then, the patient may already connect himself to the connector 208 after 4 minutes of priming and then go to bed, while the machine produces the first fill volume. It is noted that there is normally about 2 to 4 dl of solution left in the heater bag, in order to prevent complete emptying of the heater bag, because there is often some air or gas in the top of the heater bag, which should not be delivered to the patient. The first priming solution may be different from the treatment solution, for example comprising physiological sodium chloride.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for sterilizing a heat sensitive fluid in a medical solution comprising providing a first heat sensitive fluid component, providing a second fluid component, heating said second fluid component to a first temperature, said first temperature being greater than a predetermined sterilizing temperature, mixing said first heat sensitive fluid component with said heated second fluid component, whereby said first heat sensitive fluid component is heated and said heated second fluid component is cooled, and a mixed fluid is provided at a second temperature, said second temperature being at least said predetermined sterilizing temperature, and maintaining said mixed fluid at said second temperature for a predetermined sterilizing period, whereby a predetermined sterilizing dose is obtained for delivery to a recipient.

2. The method of claim 1 including controlling said heating of said second fluid component to said first temperature to ensure that said mixed fluid reaches said second temperature.

3. The method of claim 1 including cooling said mixed fluid.

4. The method of claim 1 wherein said first heat sensitive fluid component comprises a component selected from the group consisting of glucose and a glucose polymer.

5. The method of claim 1 wherein said second fluid component comprises water.

6. The method of claim 5 wherein said second fluid component includes electrolytes.

7. The method of claim 6 wherein said electrolytes are selected from the group consisting of sodium chloride, calcium chloride, magnesium chloride, potassium chloride, sodium bicarbonate, and sodium lactate.

8. The method of claim 1 including preheating said first heat sensitive fluid component.

9. The method of claim 1 including maintaining said first heat sensitive fluid component and said second fluid component under a predetermined pressure sufficient to prevent boiling of said first heat sensitive fluid component and said second fluid component.

10. The method of claim 9 wherein said providing of said first heat sensitive fluid component and providing of said second fluid component comprises providing flows of said fluid components.

11. The method of claim 10 wherein said flow of said first heat sensitive fluid component comprises a first flow rate and said flow of said second fluid component comprises a second flow rate, said second flow rate being greater than said first flow rate.

12. The method of claim 10 including determining said first and second flow rates by means of a weighing device or a flow meter, and maintaining said first heat sensitive fluid component and said second fluid component at said predetermined pressure by means of a pump.

13. The method of claim 10 wherein said heat sensitive fluid component comprises a complex fluid comprising a plurality of first fluid components including said first heat sensitive fluid component, and including sequentially sterilizing said plurality of first fluid components.

14. The method of claim 13 including providing a plurality of sources of concentrate fluid components for each of said plurality of first fluid components, providing a source of said second fluid component, said second fluid component comprising water, pumping one of said plurality of sources of said concentrate fluid components so as to increase the pressure thereof, pumping said water so as to increase the pressure thereof, and repeating said method for each of said plurality of first fluid components.

15. The method of claim 14 including preheating each of said plurality of first fluid components before said mixing with said heated second fluid component.

16. The method of claim 15 wherein said preheating comprises heat exchanging each of said plurality of said first fluid components with said predetermined sterilized dose.

17. The method of claim 16 wherein said preheating comprises initially heating said second fluid component by heat exchange with said predetermined sterilized dose, and further preheating said second fluid component to said first temperature by means of a separate heater.

18. The method of claim 17 wherein said separate heater comprises an electric heater.

19. The method of claim 18 including controlling said further preheating of said second fluid component by means of a temperature sensor downstream of said maintaining of said mixed fluid at said second temperature, whereby said second temperature is maintained at said at least said predetermined sterilizing temperature.

20. The method of claim 1 including dissolving at least one powdered substance in said second fluid component to provide at least one of said first heat sensitive fluid components and said second fluid component.

21. The method of claim 1 including providing a third heat sensitive fluid component, and mixing said first heat sensitive fluid component and said third heat sensitive fluid component with said heated second fluid component.

22. The method of claim 21 wherein said third heat sensitive fluid component comprises water and at least one amino acid.

23. Apparatus for sterilizing a heat sensitive fluid in a medical solution comprising a first vessel containing a first heat sensitive fluid component, a second vessel containing a second fluid component, a first heater for heating said second fluid component to a first temperature, said first temperature being greater than a predetermined sterilizing temperature, mixing means for mixing said first heat sensitive fluid component with said second fluid component to obtain a mixed fluid at a second temperature at least equal to said predetermined sterilizing temperature, and residence means for maintaining said mixed fluid at said second temperature for a predetermined sterilizing period, whereby a sterilized fluid is provided for delivery to a recipient.

24. The apparatus of claim 23 including a controller for controlling said first heater to obtain said first temperature.

25. The apparatus of claim 23 including a cooler for cooling said mixed fluid.

26. The apparatus of claim 23 wherein said first heat sensitive fluid component comprises a component selected from the group consisting of glucose and a glucose polymer.

27. The apparatus of claim 23 wherein said second fluid component comprises water.

28. The apparatus of claim 27 wherein said second fluid component includes an electrolyte.

29. The apparatus of claim 28 wherein said electrolyte is selected from the group consisting of sodium chloride, calcium chloride, magnesium chloride, potassium chloride, sodium bicarbonate and sodium lactate.

30. The apparatus of claim 23 including a preheater for preheating said first heat sensitive fluid component.

31. The apparatus of claim 23 including pressurizing means for maintaining said first heat sensitive fluid component and said second fluid component at a predetermined pressure to prevent said first heat sensitive fluid component and said second fluid component from boiling.

32. The apparatus of claim 23 wherein said first heat sensitive fluid component and said second fluid component comprise fluid flows.

33. The apparatus of claim 32 wherein said fluid flow of said first heat sensitive fluid component has a first flow rate and said fluid flow of said second fluid component has a second flow rate, said second flow rate being greater than said first flow rate.

34. The apparatus of claim 33 including flow rate determining means for determining said first and second flow rates, said pressurizing means comprising a pump.

35. The apparatus of claim 34 wherein said flow rate determining means comprises a weighing device or a flow meter.

36. The apparatus of claim 32 wherein said first heat sensitive fluid component comprises a plurality of first fluid components including said first heat sensitive fluid component, and including means for sequentially sterilizing each of said plurality of first fluid components and said second fluid component.

37. The apparatus of claim 36 wherein said means for sequentially sterilizing includes supply means for supplying said plurality of first fluid components, said first vessel comprising a plurality of containers for concentrates of said plurality of first fluid components, said second vessel comprising an inlet for said second fluid component, a concentrate pump for pumping one of said plurality of first fluid components from one of said plurality of containers whereby the pressure of said one of said first fluid components is increased, a water pump for pumping said second fluid component, said second fluid component comprising water, whereby the pressure of said second fluid component is increased, said heater comprising a water heater for heating said second fluid component to said first temperature, said mixing means comprising a mixer for mixing said one of said plurality of first fluid components and said heated second fluid component to provide said mixed fluid, said residence means comprising means for maintaining said mixed fluid at said first temperature for a predetermined sterilizing period to provide a sterilized dose for delivery to a recipient, and including control means for controlling and repeating said sequential sterilizing of each of said plurality of first fluid components to provide a final sterilized complex fluid.

38. The apparatus of claim 37 including preheating means for preheating said one of said plurality of first fluid components.

39. The apparatus of claim 38 including a heat exchanger for recovering heat from said sterilized dose.

40. The apparatus of claim 39 wherein said heat exchanger preheats said second fluid component by heat exchange with said sterilized dose, and including a heater for heating said second fluid component to said first temperature.

41. The apparatus of claim 40 including a temperature sensor downstream of said residence means for controlling said heater, whereby said first temperature comprises a temperature at least sufficient to constitute said sterilizing temperature.

42. The apparatus of claim 23 wherein at least one of said first and second vessels includes at least one powdered substance for dissolution in water to provide at least one of said first and second fluids.

43. The apparatus of claim 23 including a third vessel for containing a third heat sensitive fluid component.

44. The apparatus of claim 43 wherein said third heat sensitive fluid component comprises water and at least one amino acid.

* * * * *